United States Patent [19]

Meares et al.

[11] 4,339,426

[45] Jul. 13, 1982

[54] BLEOMYCIN ANALOG

[75] Inventors: Claude F. Meares; Leslie D. Anderson, both of Davis, Calif.

[73] Assignee: Regents of the University of California, Berkeley, Calif.

[21] Appl. No.: 131,685

[22] Filed: Mar. 18, 1980

[51] Int. Cl.$^3$ .................... A61K 49/00; A61K 43/00
[52] U.S. Cl. .................... 424/1; 260/112 R; 260/112.5 R; 424/9
[58] Field of Search .................. 424/1, 9; 260/112 R, 260/112.5 R

[56] References Cited

U.S. PATENT DOCUMENTS

| | | | |
|---|---|---|---|
| 3,886,133 | 5/1975 | Umezawa et al. | 260/112.5 R |
| 3,932,374 | 1/1976 | Umezawa et al. | 260/112.5 R |
| 3,957,963 | 5/1976 | Salmon et al. | 424/1 |
| 3,960,834 | 6/1976 | Umezawa et al. | 260/210 AB |
| 4,057,618 | 11/1977 | Salmon et al. | 424/1 |

OTHER PUBLICATIONS

Krejcarer et al., Biochem. Biophys. Res. Comm., vol. 77, (1977), 581–585.
Lin et al., J. Nucl. Med., vol. 15, (1974), 338–342.
Ryo et al., J. Nucl. Med., vol. 16, (1975), 127–131.
Renault et al., Chemie Therapeutique, vol. 7, (1972), 232–235.
Hall et al., J. Nucl. Med., vol. 15, (1974), 498.
Fujii et al., J. Antibiotics, vol. XXVI, (1973), 398–399.
Fujii, Bleomycin's Chemical, Biochemical, Biological Aspects, Springer Verlag, N.Y., (1979), pp. 343–344.
Umezawa, Purg. Appl. Chem., vol. 28, (1971), 665–680.
Kono et al., Chem. Pharm. Bull., 25(7), 1725–1731, (1977).
Novel, Gann Monograph on Cancer Research, 19, (1976), 301–316.
Lilien et al., Cancer, vol. 35, (1975), 1036–1049.
Yeh et al., J. Radio Anal. Chem., vol. 53, (1979), 327–336.
De Riemer et al., J. Med. Chem., vol. 22, (1979), 1019–1023.
Yeh et al., Analytical Biochem., vol. 100, (1979), 152–159.
Meares et al., Proc. Nat'l. Acad. Sci. U.S.A., vol. 73, (1976), 3803–3806.

*Primary Examiner*—Christine M. Nucker
*Attorney, Agent, or Firm*—Phillips, Moore, Lempio & Majestic

[57] ABSTRACT

Bleomycin's affinity for tumorous tissue and its ability to complex with cobalt has lead to its use in vivo as a complex with $^{57}$Cobalt. This complex has given excellent tumor images and has been useful for diagnostic purposes. Unfortunately, $^{57}$Co has the undesirable property of a 270 day half-life. The present invention provides a bleomycin analog which has a powerful meal-chelating substituent covalently bound to and chemically modifying a bleomycin. However, the inclusion of this chelating substituent in the bleomycin analog does not significantly modify the in vivo biological properties thereof with respect to unmodified bleomycin. The inventive bleomycin analog forms stable chelates with a variety of metal ions, and is particularly useful when labelled with radionuclides having short half-lives. So labelled, the bleomycin analog may be utilized for diagnostic purposes.

20 Claims, No Drawings

BLEOMYCIN ANALOG

BACKGROUND OF THE INVENTION

1. Field Of The Invention

This invention relates generally to bleomycins, and more particularly to bleomycin analogs, useful as radiopharmaceuticals, which have a metal-chelating substituent covalently bound to and modifying a bleomycin.

The invention described herein was made in the course of, or under, a grant from the National Institutes of Health.

2. Description Of The Prior Art

Bleomycins are anti-tumor antibiotics discovered by Hamao Umezawa, et al and reported in *Journal of Anti-Biotics* 19A, page 200 (1966).

Commercially available bleomycin is a mixture of bleomycins which differ only in a terminal amine. For example, the terminal amine of bleomycin $A_2$ is a 3-dimethyl-sulfopropylamino moiety whereas the terminal amine of bleomycin $B_2$ is a 4-guanidinobutylamino moiety. However, as used hereinafter, the general term "bleomycin" shall include mixtures of bleomycins; whereas when reference to a specific type, differing at the terminal amine, is preferred, such type shall be indicated.

Bleomycin's affinity for tumorous tissue, coupled with its ability to complex with a variety of metal ions, has aroused considerable interest in its potential as a tumor visualizing agent. The rationale behind this has been that the bleomycin complex of a gamma-ray emitting metal ion would localize in tumor tissue in vivo; the size and location of malignant tissue could then be determined for diagnostic purposes. $^{57}$Co-bleomycin was the first bleomycin complex to be used clinically as a tumor locating agent. Because of the 270 day radioactive half life of $^{57}$Co, several other bleomycin-metal complexes have since been investigated.

$^{67}$Ga, $^{59}$Fe and $^{62}$Zn are all poorly complexed by bleomycin. Labeling of bleomycin with $^{59}$Fe(III) has been attempted; however, Fe(III) is readily hydrolyzed in neutral aqueous solution and determined not to be bound to bleomycin. Ga(III)-bleomycin has been determined to be unstable in neutral and alkaline solutions. In vivo studies in tumor bearing mice have also demonstrated the instability of the $^{67}$Ga(III)-bleomycin complex. In a comparative study of the $^{57}$Co, $^{62}$Zn and $^{111}$In complexes of bleomycin, it has been found that the tissue distribution of $^{62}$Zn following injection of the $^{62}$Zn-bleomycin complex mimicked that of an injection of $^{62}$ZnCl$_2$, which suggests that the $^{62}$Zn-bleomycin complex dissociates in vivo.

Mixed reports have been given concerning the ability of bleomycin to complex with $^{99m}$Tc, as formation of the $^{99m}$Tc-bleomycin complex is very dependent upon the pH and concentration of reducing agent present. It is unlikely that the $^{99m}$Tc-bleomycin chelate remains intact in vivo as $^{99m}$Tc appears to be associated with human serum albumin 4 hours after injection of $^{99m}$Tc-bleomycin.

The bleomycin chelate of $^{111}$In(III) has received a great deal of attention. However, it has been shown that $^{111}$In(III) does not remain bound to bleomycin in vivo. Within four hours after injection of $^{111}$In-bleomycin, $^{111}$In has been found bound to serum transferrin in human subjects.

Encouraging clinical results have been obtained with the $^{57}$Co-bleomycin complex. The distinguishing feature of Co-bleomycin, as opposed to the other metal ion-bleomycin complexes hereto known is the stability of the complex. Although the complex is prepared by combining CoCl$_2$ with bleomycin, chelated Co(II) may be air oxidized to give Co(III). Complexes of the latter are inert to ligand exchange. Co-bleomycin has been shown to be inert and stable in vivo.

Thus, of all the metal ion-bleomycin chelates which have been known, only that of $^{57}$Co has been found to remain intact in vivo. Apparently as a result of this stability, $^{57}$Co-bleomycin has given excellent tumor images. While its chemical inertness and in vivo behaviour would appear to make $^{57}$Co-bleomycin an ideal compound for tumor imaging, $^{57}$Co has the undesirable physical property of a 270 day radioactive half-life. Ideally, a radionuclide used for diagnostic purposes should have a half-life of several hours to a few days and should emit only gamma radiation, with energy between 100 and 400 KeV. The longer lived radionuclides, such as $^{57}$Co, pose serious contamination and health problems. Unfortunately, none of the other isotopes of cobalt have the desired physical properties.

SUMMARY OF THE INVENTION

Accordingly, it is an object of the present invention to provide bleomycin analogs which retain the tumor localizing properties of bleomycin and of Cobalt(III)-bleomycin complex.

It is a further object of the present invention to provide stable biologically active bleomycin analogs which may be chelated with short-lived radionuclides.

These and other objects of the present invention are provided by a bleomycin analog comprising bleomycin which is modified in one region. The one region, as modified, is of the structure

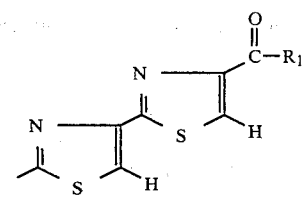

wherein $R_1$ includes a chelating substituent. Preferred chelating substituents include EDTA or DTPA derivatives.

DETAILED DESCRIPTION OF THE PREFERRED EMBODIMENTS

The present invention is a bleomycin analog which comprises a bleomycin having been modified at the terminal amine so as to include a chelating substituent. Several precursor compounds of the inventive bleomycin analog, although known to the art, shall first be briefly described for clarity and to facilitate understanding of the present invention. A detailed description of the inventive bleomycin analog, and then a method in accordance with the present invention, shall then follow.

PRECURSOR COMPOUNDS

Bleomycin has a structure illustrated below by Formula 1.

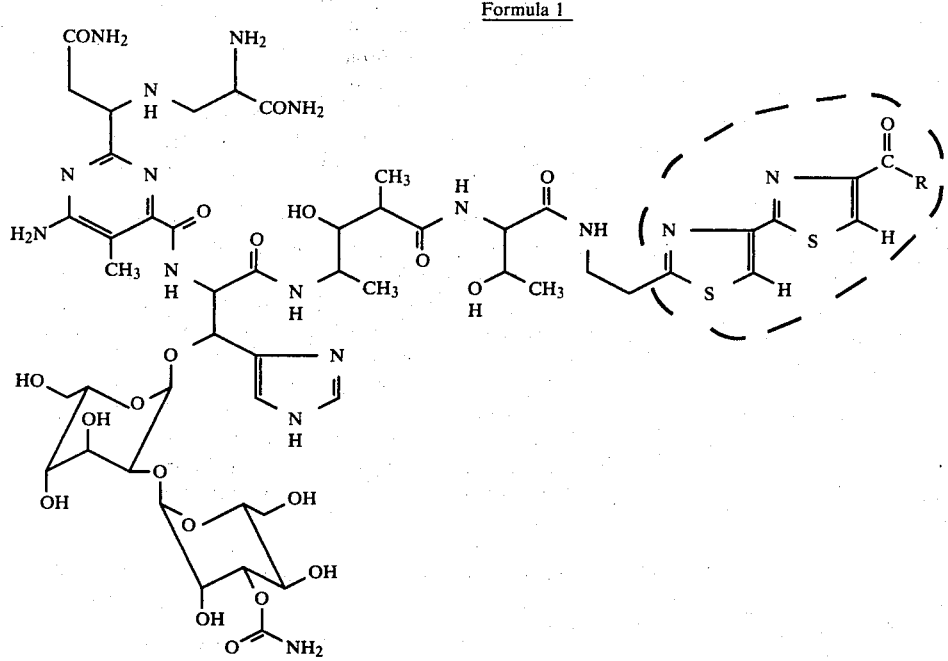

Formula 1

A dashed line has been added to the structure of bleomycin, illustrated by Formula 1 above, in order to focus upon a one region of bleomycin. This one region includes two thiazole moieties, a carbonyl moiety, and an R moiety. The R is commonly referred to as the terminal amine group of bleomycin. More particularly, in bleomycin $A_2$, R is as represented by Formula 2;

Formula 2

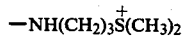

Whereas, in bleomycin $B_2$, R is as illustrated by Formula 3.

Formula 3

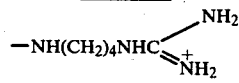

BLEOMYCIN ANALOGS

A bleomycin analog in accordance with the present invention may be formed from any of the bleomycins (which differ at the terminal amine), although it is preferred that either bleomycin $A_2$ or bleomycin $B_2$ be utilized as the precursor compound. The coined word "BLEDTA" shall be occasionally used herein to indicate a bleomycin analog in accordance with the present invention. Examples of forming the inventive bleomycin analog from both bleomycin $A_2$ and bleomycin $B_2$ shall be hereinafter described.

In the best mode contemplated for forming bleomycin analogs, bleomycin $A_2$ is the preferred precursor compound. Formation of the bleomycin analog in accordance with the present invention is wherein the terminal amine of bleomycin $A_2$ has been chemically modified or entirely removed; whereas, formation of the bleomycin analog from bleomycin $B_2$ is wherein the terminal amine has been entirely removed.

Whichever is the precursor, bleomycin must be modified so as to include a chelating substituent with a plurality of functional groups capable of chelating metal ions. It has been found that the transport properties and tumor concentrating ability of bleomycin analogs in accordance with the present invention are retained despite modification (or replacement) of the terminal amine and inclusion of the chelating substituent.

The modified one region of bleomycin is of the structure as illustrated by Formula 4, below.

Formula 4

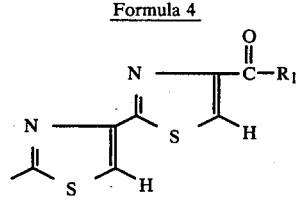

The two thiazole moieties of this one region, the carbonyl moiety, and the remainder of the unmodified bleomycin molecule are equivalent to (that is, originate from) a presursor bleomycin molecule.

The chelating substituent included in the $R_1$ moiety has a powerful, metal-chelating one portion, distal with respect to the carbonyl moiety of the modified one region, and has another portion which is covalently bound adjacent the carbonyl moiety.

This metal-chelating portion shall next be more fully described, and the other, or covalent binding portion, shall be more fully described thereafter.

METAL-CHELATING ONE PORTION

The metal-chelating one portion of the chelating substituent must be capable of forming a stable chelate with metal ions. Sufficient stability is herein defined as being about comparable to the in vivo stability of the $^{57}$Co-bleomycin complex known to the prior art.

Preferred chelating substituents include EDTA or DTPA derivatives. As used herein, EDTA is a short-hand term for ethylenediaminetetraacetic acid and DTPA is a short-hand term for diethylenetriaminepentaacetic acid. These EDTA and DTPA derivatives include a plurality of carboxylate moieties and amino moieties capable of chelating a great variety of metal ions. That is, the carboxylate groups and amino groups of these EDTA and DTPA derivatives function as the metal-chelating one portion of the chelating substituent.

The EDTA derivatives suitable for the present invention are 1-substituted EDTA derivatives where the four carboxylate groups of the familiar EDTA structure are present; or, where one of the carboxylate groups has been replaced with an alcohol group. Thus, a 1-substituted EDTA derivative useful in the present invention has a partial structure (that is the metal-chelating one portion) as illustrated by Formula 5, below.

The reason for having one carboxylate moiety optionally replaced with an alcohol moiety is to permit the electric charge of the metal chelate to be zero when a metal ion having a $+3$ charge is coordinated with the carboxylate moieties, rather than $-1$ as would otherwise be the case. Such a neutral charge is believed to be useful in increasing tumor uptake properties of the inventive BLEDTA.

The DTPA derivatives suitable for the present invention are substituted DTPA derivatives, preferably wherein the substituent thereof includes a phenyl moiety having a para-substituted functional group on the phenyl moiety. For example, a preferred functional group on the phenyl moiety is bromoacetamide.

Among the metal ions which may be stably chelated by the chelating substituent of the bleomycin analog are the ionic species of those elements illustrated by Chart or Formula 6, below.

Formula 6

|    |    |    |    |    |    |    |    | 13 Al |    |    |
|----|----|----|----|----|----|----|----|-------|----|----|
|    | 24 Cr |    | 26 Fe | 27 Co | 28 Ni | 29 Cu |    | 31 Ga |    |    |
| 39 Y | 40 Zr |    | 43 Tc | 44 Ru | 45 Rh | 46 Pd |    | 49 In | 50 Sn |    |
| 57 La | 72 Hf |    |    | 76 Os | 77 Ir |    | 80 Hg |    |    | 83 Bi |
| 89 Ac |    |    |    |    |    |    |    |    |    |    |

| 58 Ce | 59 Pr | 60 Nd | 61 Pm | 62 Sm | 63 Eu | 64 Gd | 65 Tb | 66 Dy | 67 Ho | 68 Er | 69 Tm | 70 Yb | 71 Lu |
|-------|-------|-------|-------|-------|-------|-------|-------|-------|-------|-------|-------|-------|-------|
| 90 Th | 91 Pa | 92 U | 93 Np | 94 Pu | 95 Am | 96 Cm | 97 Bk | 98 Cf | 99 Es | 100 Fm | 101 Md | 102 No | 103 Lw |

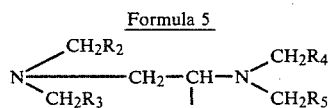

Formula 5

As illustrated by Formula 5, above, three of the $R_2$–$R_5$ groups are carboxylate moieties, whereas the remaining one of said $R_2$–$R_5$ groups is either a carboxylate moiety or an alcohol (—$CH_2OH$) moiety. When the remaining one of the $R_2$–$R_5$ groups is preferred to be an alcohol (—$CH_2OH$) moiety, the chelating agent used to form the chelating substituent will usually have been prepared from an alpha amino acid precursor, as is disclosed by a copending application Ser. No. 06/131,684, filed on even date with this application, entitled "Chelating Agents And Method", inventors Meares, et al, the disclosure thereof incorporated herein by reference.

More preferred, for radiopharmaceutical labelling uses, are radionuclides, preferably which emit gamma radiation and have half-lives ranging from about three hours to about three days. $^{111}$Indium, $^{99m}$Technetium (metastable), and $^{68}$Gallium are most preferred radionuclides. Also, for in vitro studies, the luminescent terbium (III) or europium (III) ions are especially useful.

OTHER COVALENT BINDING PORTION

The 1-substituent of the EDTA derivatives (that is, the other, or covalent binding portion) includes phenyl and benzyl derivatives. Particularly preferred as the chelating substituent are those phenyl derivatives chosen from the class of 1-(p-aminophenyl)-EDTA derivatives. For example, a 1-(p-bromoacetamidophenyl)-EDTA derivative forms a BLEDTA with the modified one region of the structure as represented by Formula 7a, below.

Formula 7a

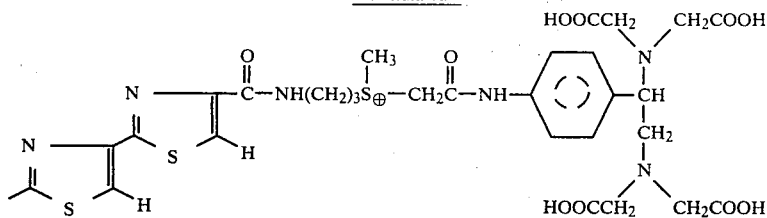

Among the particularly preferred chelating agents to form substituents with bleomycin are also EDTA derivatives, or analogs, formed from alpha amino acid and alpha amino acid amide precursors, and a particularly preferred one of such EDTA alpha amino acid precursor analogs has recently been found to be L-p-bromoacetamidobenzyl EDTA, which is prepared as is disclosed by the previously noted copending application herewith, entitled "Chelating Agents And Methods", inventors Meares, et al., and which may be utilized to form a BLEDTA with the modified one region of the structure as represented by Formula 7b, below.

This amino compound was dissolved in 500 μL of $H_2O$ and neutralized; then bromoacetylbromide (20 μL, 230 μmol) was added in 5 μL portions until the solution was negative to fluorescamine. Excess bromoacetyl bromide and bromoacetic acid were removed by repetitively extracting the acidic reaction mixture with diethyl ether. The organic layer was tested with 4-(p-nitrobenzyl)-pyridine to follow the course of the extraction. The pH of the aqueous layer was adjusted to 2.3 with 6 N HCl and the solution was left on ice overnight. The resulting precipitate, 1-(p-bromoacetamidophenyl), was washed with ice cold 0.01 M HCl and dried on a vac- Formula 7b

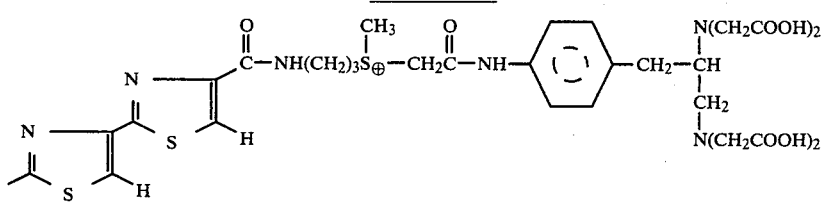

PREPARATION OF BLEDTA

A BLEDTA, modified in the one region thereof as represented by Formula 7a and 7b above, may be made from bleomycin $A_2$ as the precursor compound.

The BLEDTA as in Formula 7a shall be described by Examples I and II, wherein: Subpart(a) of Example I describes the preparation of 1-(p-bromoacetamidophenyl)-EDTA, which is a preferred chelating agent; Subpart(b) of Example I describes the preparation of bleomycin $A_2$ complexed with cobalt(III) prior to modification of the one region thereof; Subpart(c) of Example I describes a chemical modification of the cobalt-(III)-bleomycin $A_2$ of subpart(b) at the terminal amine thereof; and, Subpart(d) of Example I then describes the preparation of the final product, which is a bleomycin analog in accordance with the present invention.

Example III describes the preparation of the BLEDTA as represented by Formula 7b wherein: Subpart (a) of Example III describes the preparation of 1-(p-bromoacetaminobenzyl)-EDTA, which is a preferred chelating agent, from p-aminobenzyl EDTA; and Subpart (b) of Example III then describes the preparation of the final product, which is a bleomycin in accordance with the present invention.

EXAMPLE I

Subpart(a): Preparation of 1-(p-bromoacetamidophenyl)-EDTA 1-(p-bromoacetamidophenyl) EDTA was prepared by dissolving 100 mg (240 μmol) of 1-(p-nitrophenyl)-EDTA in 50 mL of aqueous NaOH (such that the final pH was 11.4) and 29 mg of 10% Pd/C was added. Reduction was carried to give 1-(p-aminophenyl)-EDTA.

uum line. The yield was 69.03 mg (137 μmol, 57%). Anal. ($BrC_{18}H_{22}N_3O_9$) Br, C, H, N.

(Subpart(b): Preparation of Co.Bleo $A_2$

Bleomycin was obtained from Bristol Laboratories, Cyracuse, New York (Trademark BLENOXANE). A substantially neutral, aqueous solution containing the bleomycin and a slight excess of cobalt chloride was saturated with oxygen to generate a cobalt (III)-bleomycin complex as follows.

1.16 mL of a 0.100 solution of $CoCl_2$ was added to 16.4 mL of a 10 mg/mL solution of bleomycin (0.11 mmol) and the pH was adjusted to 6.5 with 25 μL of 6 M NaOH. The solution was placed in a 500 mL container and saturated with $O_2$. The container was capped, and the solution was left at 50° C. overnight. Co (III)-bleomycin $A_2$ was isolated from the solution by cation exchange chromatography.

It was found that the cobalt (III)-bleomycin $A_2$ isolated from the solution of Example 1 was eluted as two distinct peaks having different colors: green and orange. Green cobalt (III)-bleomycin $A_2$ was unstable with respect to the orange form, and if left at room temperature, aqueous solutions thereof would convert to a mixture of orange and green. This conversion could be accelerated by heating. Except as further specifically mentioned hereinafter, the more stable orange form was isolated and utilized in the chemical modifications of Co(III)-bleomycin $A_2$.

The Co-(III)-bleomycin $A_2$ solution, above, was heated for three hours at 110° C. to partially convert the green form to the orange form. This mixture was then applied to a column packed with a carboxymethyl cross-linked dextran cation exchanger (NH4+form, 1×79 cm) and eluted with a gradient of 0.01 to 0.5 M ammonium formate, pH 6.5. The orange and green forms were eluted with an ammonium formate concentrations of 0.25 and 0.28 M, and the solutions were lyophilized to remove salt. The yield was 35 mg (22 μmol) of orange Co(III)-bleomycin A2 (which has a terminal amine represented by FIG. 2 previously described).

Subpart(c): Preparation of Co.Bleo DMA2 was eluted with 0.06 M ammonium formate, and lyophilized 2 days to remove the salt. The yield was determined to be 4.96 μmol (30%) by measuring the absorbance at 452 nm of an aqueous solution of the product ($\epsilon_{452}=214$ M$^{-1}$ cm$^{-1}$). The product had $R_f$ 0.50; autoradiography of the TLC plate of the $^{111}$In complex of the product indicated that >88% of the radioactivity on the plate was present in a spot with $R_f$ 0.50.

The product from Example I, subpart(d), is a bleomycin analog in accordance with the present invention whose full structure is as represented by Formula 9(a), below.

Formula 9(a)

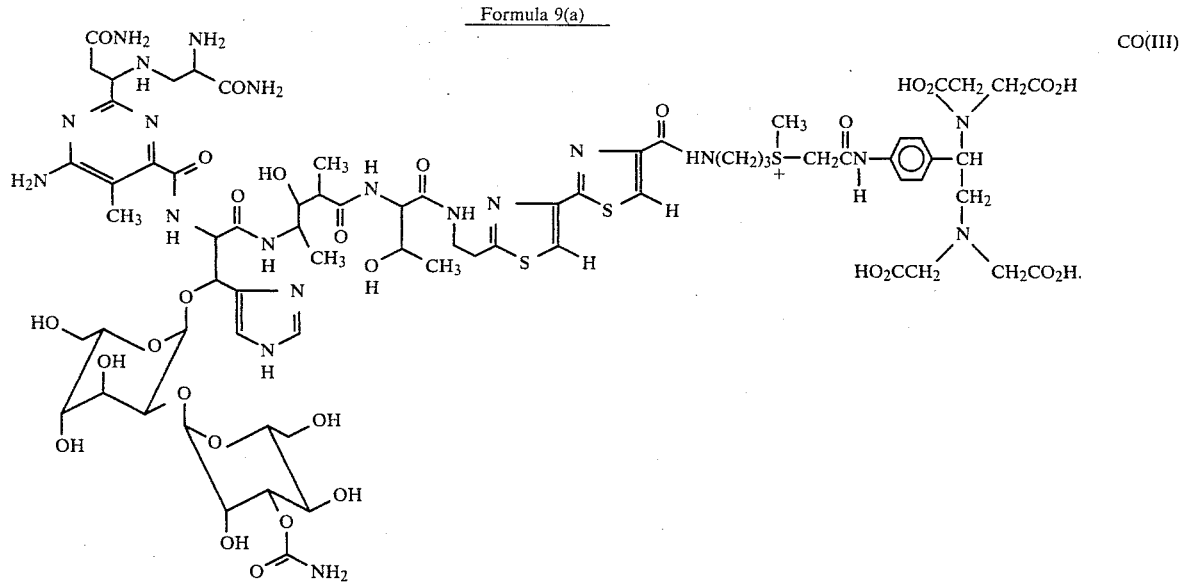

The Co(III)-bleomycin A2 produced by subpart(b), above, was demethylated at the terminal amine by reaction with sodium methyl- or ethyl mercaptide in methanolic solution and purified by cation exchange chromotography to yield a Co(III)-bleomycin demethyl A2 whose terminal amine is as represented by Formula 8.

FORMULA 8

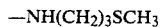

As proof of identity, this demethylated Co(III)-bleomycin A2 compound was methylated with CH3I to yield the Co(III)-bleomycin A2 of subpart(b), which was confirmed by HPLC and TLC. The 360 MH3 NMR spectrum also confirmed that the compound was Co.BleoDMA2.

Subpart(d): Preparation of BLEDTA I 16.5 μmol of the demethylated Co(III)-bleomycin A2 from subpart(c) above was combined with 165 μmol of the 1-(p-bromoacetamidophenyl)-EDTA of subpart(a) above. This gave 5 mL of aqueous solution, which was adjusted to pH 4.3 by the addition of 15 μL of 6 N NaOH. This mixture was reacted at room temperature for 7.5 h; 84% of the demethylated Co(III)-bleomycin had reacted as determined by HPLC. The pH of the mixture was adjusted to 8.1 with 6 N NaOH and the solution was applied to anion exchange column (1×67 cm, formate form). The column was washed with 0.01 M ammonium formate, pH 8.1, followed by a gradient of 0.01 to 0.1 M ammonium formate, pH 8.1. Product The precursor bleomycin, for example the precursor bleomycin A2 described in Example I, and the resultant BLEDTA, both have another (unmodified) region with an intrinsic metal binding capacity. Thus, subpart(b) of Example I described the formation of a cobalt complex with bleomycin. The cobalt remained complexed with the BLEDTA. The cobalt was bound, or complexed, with the precursor bleomycin, and the bleomycin analog, in this other region thereof. It is believed that six nitrogen ligands, including the imidazole and pyrimidine moieties of bleomycin provide this intrinsic metal binding.

Although a bleomycin analog in accordance with the present invention may be complexed with cobalt in the other region, the inventive bleomycin analogs need not be so complexed, or may be complexed with metal ions other than cobalt. Example II illustrates BLEDTA in complex with copper and with copper removed.

EXAMPLE II

A bleomycin mixture (trademark Blenoxane) was obtained from Bristol Laboratories. This was mixed with a slight molar excess of aqueous copper(II) chloride and fractionated on a cation-exchange column. The A2 fraction was lyophilized and then pyrolyzed at 100° C. and 2 torr for 3 hours, converting it to bleomycin-demethyl A2. This product was purified using a cation-exchange column and a linear 0.01 M to 0.5 M gradient of ammonium formate. A 65% overall yield of bleomycin-demethyl A2 (copper complex) was obtained; the chromatographic and spectroscopic properties of this material were in agreement with literature values.

An acidic aqueous solution of 1-(p-bromoacetamidophenyl)-EDTA, as described in Example I, subpart (a) above, was adjusted to pH 4.8 by addition of 1 M sodium citrate, and a 5% molar excess of 2 M CuCl₂ was added (resulting pH=3.7). To this solution was added 0.04 mmol of the copper-complexed bleomycin-demethyl A₂ (final pH=4.0); the resulting deep blue solution was stirred for 6 hours at 37°. The progress of this reaction was monitored by thin-layer chromatography on silica gel using a solvent containing equal volumes of methanol and 10% aqueous ammonium acetate. Three fluorescence-quenching spots were observed: bleomycin ($R_f$=0.8), 1-(p-bromoacetamidophenyl)-EDTA ($R_f$=0.9), and product ($R_f$=0.5).

The reaction mixture was fractionated on a 1.5×40 cm anion-exchange column using a 0.01 M to 1.0 M gradient of ammonium formate. Two components were found with $R_f$=0.5. The complexed copper of the products (both bleomycin analogs analogous to that illustrated by Formula 9a, above, but with complexed copper rather than complexed cobalt) was extracted with dithizone or oxine to yield two bleomycin analogs with no metal ion complexed at the intrinsic metal binding site. Such uncomplexed BLEDTA shall be hereinafter referred to as Formula 9(b) and 9(c) compounds illustrated below.

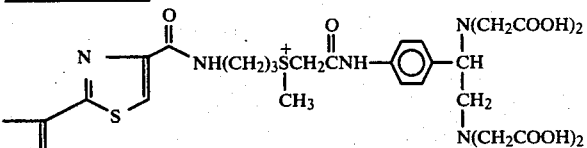

Formula 9(b)

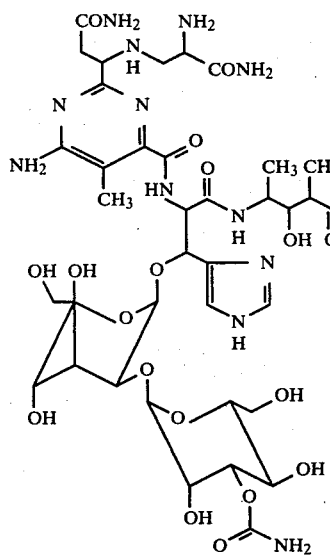

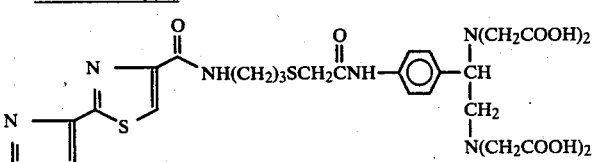

Formula 9(c)

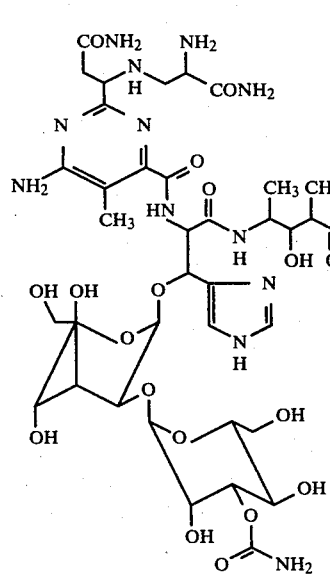

Example II illustrates that copper is first complexed with the bleomycin precursor and then removed from the bleomycin analog. This is done as it has been found that otherwise the chelating substituent tends to be attached to the bleomycin precursor at sites other than the one region.

EXAMPLE III

Subpart (a): Preparation of 1-(p-bromoacetamidobenzyl)-EDTA 303.5 μmole of p-aminobenzyl EDTA was dissolved in 500 μl of H₂O and the pH of the solution was adjusted to 6.5 with 20 μl of concentrated HCl. Bromoacetyl bromide was added (46 μl) until the mixture was negative to fluorescamine. This was followed by 10 extractions with 500 μl of diethyl ether to remove excess bromoacetyl bromide. After the extractions, the pH of the solution was 1.0; it was adjusted to 2.2 by the addition of 100 μl of 1 M NaOH. A white precipitate began to drop out at pH 2. The solution was placed on ice and left overnight. The mixture was then centrifuged, and the white solid washed twice with 600 μl of ice cold 0.1 M HCl. The solid was dried under vacuum. Yield was 32.07 mg (61.8 μmol; 20.4%) of p-bromoacetamidobenzyl EDTA. Thin layer chromatography of the product on silica plates with MeOH/10% aqueous NH₄OAc (50/50: v/v) showed only one spot with an R$_f$ of 0.96 which was both fluorescence quenching and 4-(p-nitrobenzyl)pyridine positive.

Subpart (b): Preparation of BLEDTA III 6.18 μmol of CoA₂DM bleomycin and 61.8 μmol of the solid product from subpart (a), above, was combined in aqueous solution with a final volume of 1.87 ml. The pH of the solution was adjusted to 4.4 by the addition of 20 μl of 6 N NaOH and 5 μl of HCl. The reaction was allowed to proceed at room temperature and was monitored by HPLC. After 6 hours, the reaction mixture was applied to an anion exchange column following adjustment of the pH to 8.2 by addition of 6 N NaOH. The 1×45 cm anion exchange column was washed with 150 ml of 0.01 M ammonium acetate, pH 8 followed by a linear gradient of 0.01 M to 0.3 M ammonium acetate, pH 8. The absorbance of every other fraction at 290 nm was determined. The product was eluted with 0.18 M ammonium acetate. Fractions containing the product were pooled and lyophilized for two days to remove solvent and excess salt. Thin layer chromatography (using the system described above) of the product showed one spot with an R$_f$ of 0.54. An autoradiogram of a thin layer chromatogram of the ¹¹¹In(III) chelate of the product also showed only one spot with R$_f$=0.4.

The 360 MHz NMR spectrum of the product clearly showed that the benzyl EDTA moiety was present and bound to the terminal amine of Co-bleomycin. A clean AB doublet centered at 7.15 ppm corresponding to the aromatic portons on the benzyl EDTA moiety was present. The position of the terminal amine methyl porton resonance (3.0 ppm downfield) indicated that the terminal amine thioether had been alkylated to give a sulfonium ion.

Yield of the product, sometimes hereinafter referred to as "BLEDTA III", was 2.83 μmoles (46%). The product from Example III, subpart (b), is a bleomycin analog in accordance with the present invention whose full structure is as represented by Formula 9(d), below.

Formula 9(d)

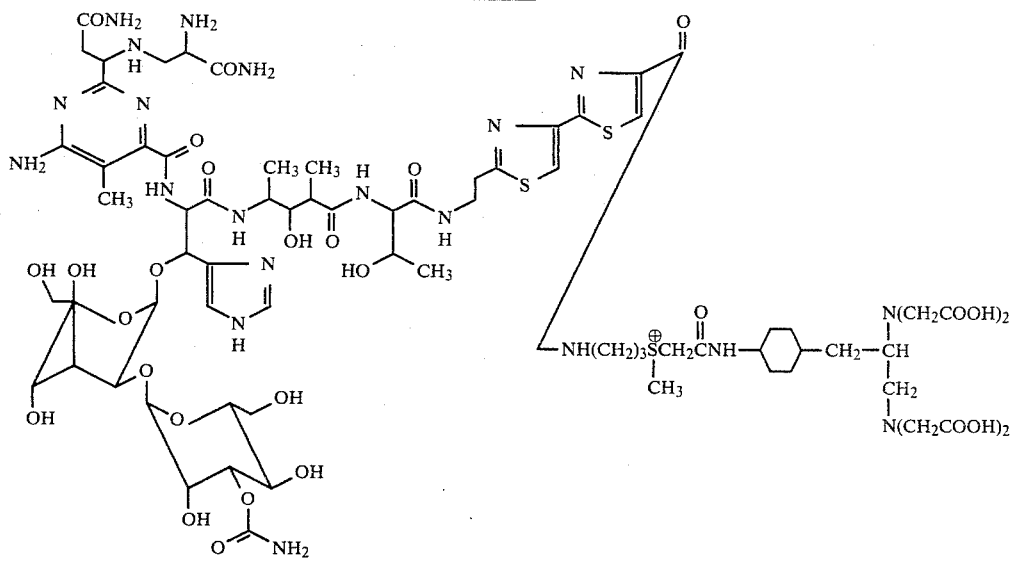

A bleomycin analog in accordance with the present invention may also utilize bleomycin B₂ as the precursor molecule. As such, bleomycinic acid may be produced from bleomycin B₂, as disclosed by U.S. Pat. No. 3,932,374, issued Jan. 13, 1976, inventors Umezawa, et al., wherein the terminal amine is entirely removed. (Alternatively, bleomycin acid may be formed from bleomycin A₂ via bleomycin demethyl-A₂ as disclosed in *Bleomycin—Chemical, Biochemical, and Biological Aspects*, Hecht, ed., Springer-Verlag, pp. 343–344 (1979).) An inventive bleomycin analog may be produced from the bleomycinic acid as follows.

Ethylenediamine is coupled to a bleomycinic acid-metallo complex (such as cobalt) in the presence of carbodiimide. The reaction product is then subsequently coupled with DTPA by the following reaction, illustrated by Formula 10 below. ("BLEO" represents the remaining, unmodified bleomycin molecule).

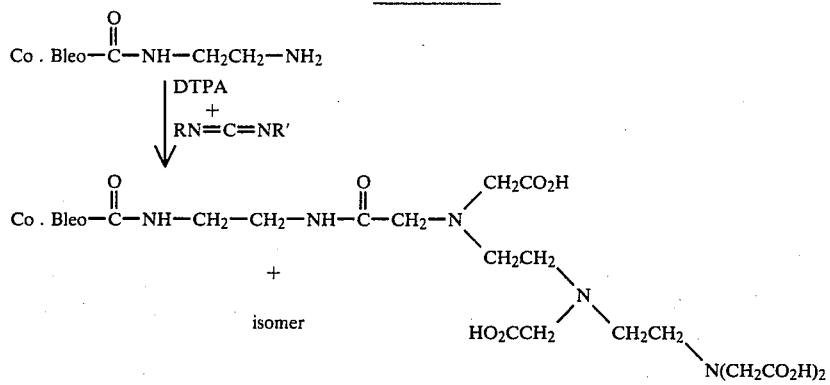

Formula 10

METHOD OF LOCALIZING TUMORS

The BLEDTA as illustrated by Formula 9(a) was utilized to localize tumors in human patients and in mice as follows. (For convenience, this bleomycin analog shall hereinafter also be referred to as BLEDTA I; and, when radiolabelled, as $^{111}$In BLEDTA I).

A citric acid solution containing $^{111}$InCl$_3$ was combined with an aqueous solution of BLEDTA I at room temperature. Labelling was monitored by TLC and was complete within 5 minutes. BALB/c mice with "KHJJ" tumor implanted in the flank were injected with the orange and green $^{57}$CO(III) complexes of bleomycins A$_2$ and B$_2$ and the $^{111}$In-labelled BLEDTA I. As control experiments, the complex ($^{111}$In-bleomycin) formed by addition of $^{111}$In$^{3+}$ to Blenoxane, a commercial mixture of bleomycins and the chelate of $^{111}$In$^{3+}$ with 1-phenyl-EDTA were also studied.

Following the injection of each radiolabelled compound into the tail veins of specifically prepared BALB/c mice, the organ distribution and tumor uptake of radioactivity were determined by the methods as described in J. Med. Chem. 17, 1304 (1974) by Sundberg, et al., incorporated herein be reference. The organic distribution and tumor uptake of radioactivity in the mice are shown in Table 1.

Tumor uptake of radioactivity after injection of $^{111}$In-BLEDTA I is more than double that observed with orange $^{57}$Co-bleomycin A$_2$; the blood, lungs, spleen, muscle and skin also showed higher uptake of radioactivity for $^{111}$In-BLEDTA I. The organ distribution of $^{111}$In-bleomycin shows very high uptake of radioactivity in the kidneys, liver, spleen and bone, which suggests dissociation of the complex in vivo. In comparison, the organ distribution of $^{111}$In-1-phenyl-EDTA shows little uptake of radioactivity in any organ except the liver and spleen, reflecting its rapid excretion.

Tumor localization by $^{111}$In-BLEDTA I was investigated in a series of patients with biopsy-proven cancer. Of the 29 patients studied, 21 had squamous carcinomas of the head and neck. Patients were scanned 18 to 24 hours after intravenous injection of one to two mCi of $^{111}$In-BLEDTA I. Whole-body scans and spot views were obtained with a gamma camera (Searle Pho-Gamma IV). Scans following injection of $^{111}$In-labelled BLEDTA I showed all the disease present for 17 of these patients. Each of the other four patients with squamous carcinoma of the head and neck had only some disease visualized. Also studied were individuals with lung cancer, unknown primary tumors, metastatic adenocarcinomas, thyroid cancer and mucoepidermoid cancer. All disease was visualized in one lung cancer patient; $^{111}$In-BLEDTA I revealsed some, but not all, of the disease in each of the other patients. The smallest tumor localized was 1 cm in diameter. TLCs of 24 hour urine showed 87% of the total radioactivity on the TLC plate moved with $R_f$ 0.5, identical to that of $^{111}$In-BLEDTA I. Ten percent of the excreted radioactivity

TABLE I

Distribution and Uptake in BALB/c Mice with KHJJ Tumor
% of injected radioactivity per gram[a]

| Organ | Green[57]CO—B$_2$[d] | Orange[57]Co—B$_2$[d] | Green[57]Co—A$_2$[b] | Orange[57]Co—A$_2$[b] | Bleomycin analog[c] | $^{111}$In-bleomycin[e] | [111]In-I-phenyl-EDTA |
|---|---|---|---|---|---|---|---|
| Blood | .024 ± .002 | .006 ± .005 | .013 ± .004 | .003 ± .001 | .55 ± .05 | .48 ± .20 | .19 ± .029 |
| Lungs | .18 ± .05 | .10 ± .003 | .10 ± .04 | .075 ± .008 | .42 ± .05 | 1.22 ± .58 | .029 ± .045 |
| Liver | .65 ± .04 | .23 ± .004 | .40 ± .11 | .20 ± .03 | .35 ± .03 | 2.77 ± 1.03 | .66 ± .43 |
| Spleen | .19 ± .03 | .12 ± .02 | .15 ± .03 | .093 ± .011 | .27 ± .03 | 1.93 ± .40 | .83 ± .65 |
| Kidneys | 2.12 ± .66 | 2.80 ± .82 | 1.43 ± .46 | 1.69 ± .33 | 1.72 ± .26 | 8.98 ± 2.24 | .22 ± .18 |
| Tumor | .54 ± .05 | .26 ± .04 | .55 ± .14 | .19 ± .03 | .68 ± .16 | 1.98 ± .38 | .098 ± .088 |
| Muscle | .017 ± .003 | .011 ± .003 | .020 ± .008 | .015 ± .008 | .063 ± .010 | .31 ± .026 | .006 ± .010 |
| Bone | .094 ± .013 | .031 ± .009 | .089 ± .048 | .035 ± .016 | .077 ± .060 | 1.26 ± .087 | .015 ± .025 |
| Skin | .066 ± .026 | .209 ± .288 | .059 ± .016 | .064 ± .009 | .21 ± .03 | 1.18 ± 1.02 | .037 ± .036 |

[a]Mean ± SD for 3 mice
[b]Co(III)-bleomycin A$_2$
[c][111]In-BLEDTA I
[d]Co(III)-bleomycin B$_2$ The in vivo distributions of green $^{57}$Co-bleomycin A$_2$ and green $^{57}$Co-bleomycin B$_2$ do not differ significantly; orange $^{57}$Co-bleomycin A$_2$ and orange $^{57}$Co-bleomycin B$_2$ also have similar organ distributions. One day after injection, the concentration of green $^{57}$Co-bleomycin A$_2$ in blood and in tumor is more than twice that or orange $^{57}$Co-bleomycin A$_2$; the same is true for the distribution of green and orange $^{57}$Co-bleomycin B$_2$.

was accounted for by a degradation product with $R_f$ 0.9, which is typical for many small indium chelates.

As shown in Table 1 for the several metallobleomycins investigated, organ distributions in tumor bearing mice show statistical differences between the green and orange forms of Co(III)-bleomycin $A_2$ (and of Co(III)-bleomycin $B_2$). However, the different terminal groups do not appear to have an important effect. The structural differences between the green and orange cobalt bleomycins almost certainly involve different coordination at cobalt; both species are diamagnetic, and the NMR spectrum of green Co(III)-bleomycin $A_2$ suggests that the methyl groups of the threonine and valeric acid residues are perturbed from their normal environments.

It is striking that the blood levels of $^{111}$In-BLEDTA I in mice are roughly two orders of magnitude higher than those of the $^{57}$Co-bleomycins studied; such a difference was not observed in human subjects. Uptake of radioactivity by the tumor and other organs of the mouse do not differ greatly for $^{111}$In-BLEDTA I as compared to the $^{57}$Co-bleomycins; however, the organ distributions of $^{111}$In-bleomycin and $^{111}$In-1-phenyl-EDTA contrast markedly with that of $^{111}$In-BLEDTA I. These results strongly suggest that the in vivo transport properties of BLEDTA I are not substantially different from those of Co(III)-bleomycin $A_2$ or Co(III)-bleomycin $B_2$. Further support is provided by the distribution and tissue concentrations of $^{111}$In-BLEDTA I in human subjects, which are similar to those previously reported for $^{57}$Co-bleomycin. All 29 patients with known cancer had at least one site of the disease visualized by $^{111}$In-BLEDTA I; this is a considerable improvement over prior art studies of a comparable series of patients using the complex formed between indium (III) and Blenoxane, in which 9 out of 29 biopsy-proven cancer cases failed to visualize at all.

The two BLEDTA's illustrated by Formulas 9(b) and 9(c) were utilized to localize tumors in mice and in rabbits. (For convenience, the bleomycin analog as in Formula 9(b) shall hereinafter be referred to as BLEDTA(A); and, when radiolabelled, as $^{111}$In-BLEDTA(A). Similarly, the bleomycin analog as in Formula 9(c) shall be referred to as BLEDTA(B); and, when radiolabelled, as $^{111}$In-BLEDTA (B).

After removal of copper by extraction with dithizone or oxine, the BLEDTA's (A) and (B) were ready for labelling with other metal ions. In order to assure that addition of a simple metal salt lead to rapid, quantitative binding of the metal ion to the EDTA group (rather than binding directly to the metal-binding region of the bleomycin, or precipitating as the metal hydroxide), the metal-complexation reaction was carried out in a buffer solution with weak metal-chelating properties.

The principal concern is that binding of the desired metal ion to the EDTA group should greatly predominate over all other possible reactions. The choice and concentration of buffer, and the pH, may be varied in order to achieve this. For example, with the addition of trivalent indium to the chelating group, it has been found that 0.1 M citrate provides a useful buffer medium for such reactions.

Although the stability constant of the chelate between indium and native bleomycin does not appear to be available for the literature, in the present invention the bleomycin moiety of BLEDTA does not compete appreciably with the EDTA moiety for binding indium in 0.1 M citrate between pH 2 and pH 4.

The two bleomycin analogs-BLEDTA(A) and (B)- were rapidly and specifically labelled with $^{111}$In$^{3+}$. A small aliquot of a dilute solution ($10^{-4}$ M) of BLEDTA(A) and (B) respectively in 0.1 M citrate (pH 2.8) was added to a container of dry $^{111}$InCl$_3$, and incubated for 5 minutes at room temperature. The solutions were then diluted with normal saline solution for injection.

Following the injection of $^{111}$In-BLEDTA(B) into the tail veins of specially prepared BALB/c mice, the organ distribution and tumor uptake of radioactivity were determined. A tumor line, "KHJJ", derived from a primary mammary carcinoma arising in a mouse and maintained for over 100 transplant generations was used for the assay. Transplantation was by subcutaneous implantation of tumor fragments about 1 mm in diameter into the flank. The studies were carried out after 14 days of growth, when the tumor had reached a size of about 1 cm$^3$. On histological examination, the tumor has a "carcinoma-like" pattern with a predominance of islands of round or polygonal malignant cells with little stroma and a generally undifferentiated appearance. After transplantation, the tumor takes in almost all animals and grows without metastasizing or killing the mice within 14 days.

For the distribution assay, a volume of 0.2 ml containing approximately 0.1 μCi of $^{111}$In-BLEDTA (B) was injected into the tail veins of five mice. After 18 hours, each mouse was anesthetized with ether, and blood was collected from the jugular vein into two preweighed capillary tubes. The mouse then was killed instantly by cervical dislocation and the major organs excised. Samples of muscle, skin, bone (left femur plus marrow), tail, and tumor also were taken. All tissue samples were weighed immediately after excision and counted in a well-type scintillation counter.

As shown in Table II, the uptake of radioactivity in liver and bone is quite low, indicating no loss of indium from the chelate. Favorable tumor/organ radioactivity concentration ratios are seen for all organs examined except the kidneys.

TABLE II

| Distribution and Uptake in BALB/c Mice with KHJJ Tumor % of injected radioactivity per gram[a] | | | |
|---|---|---|---|
| Organ | $^{111}$In-bleomycin | $^{111}$In-1-phenyl-EDTA | BLEDTA B |
| Blood | .48 ± .20 | .19 ± 0.29 | .205 ± .066 |
| Lungs | 1.22 ± .58 | .029 ± .045 | .254 ± .067 |
| Liver | 2.77 ± 1.03 | .66 ± .43 | .263 ± .068 |
| Spleen | 1.93 ± .40 | .83 ± .65 | .327 ± .088 |
| Kidneys | 8.98 ± 2.24 | .22 ± .18 | 1.023 ± .333 |
| Tumor | 1.98 ± .38 | .098 ± .088 | .393 ± .015 |
| Muscle | .31 ± .026 | .006 ± .010 | .063 ± .015 |
| Bone | 1.26 ± .087 | .015 ± .026 | .188 ± .080 |
| Skin | 1.18 ± 1.02 | .037 ± .036 | .166 ± .052 |

[a]Mean ± SD for 3 mice.

Solutions of the indium-111 chelates of BLEDTA (A) or BLEDTA (B) were injected into the ear veins of white rabbits bearing type VX2 adenocarcinomas implanted under the right foreleg and the right hind leg. Two hours after injection, and again 18 to 24 hours after injection, the rabbits were scanned with a gamma camera, which provides a two-dimensional display of the distribution of radioactivity in the body. Scans were obtained 24 hours after injection of 700 μCi of $^{111}$In-BLEDTA(A). A small tumor 1 cm in diameter under the right foreleg was clearly visualized, while a tumor 2 to 3 cm in diameter under the right hind leg was strikingly evident. Similar results were obtained with $^{111}$In- BLEDTA (B). Scans taken 24 hours after injection were superior to those taken two hours after injection because at two hours, high concentrations of radioactivity in the kidneys and bladder interfered with tumor visualization.

The bleomycin analog "BLEDTA III" was similarly tested as follows.

The $^{111}$In (III) chelate of BLEDTA III was prepared by adding $^{111}$In (III) in 0.1 M citrate to a 0.5 mM solution of BLEDTA III and allowing the solution to stand at room temperature for 5 minutes. Labeling was checked by TLC.

The distribution of $^{111}$In-BLEDTA III in BALB/c mice implanted with a KHJJ tumor in the flank and a turpentine-induced abscess was determined 24 h following intravenous injection of the $^{111}$In-BLEDTA III. The results are given in Table III below; the results of a similar experiment with $^{111}$In-BLEDTA I are shown for comparison.

TABLE III

Distribution of Radioactivity In BALB/c Mice With KHJJ Tumor % injected radioactivity/g

| Organ | $^{111}$In-BLEDTA$^a$III | $^{111}$In-BLEDTA$^c$I |
|---|---|---|
| Blood | 0.29 ± 0.03 | 0.55 ± 0.05 |
| Heart | 0.12 ± 0.02 | |
| Lungs | 0.25 ± 0.02 | 0.42 ± 0.05 |
| Liver | 0.29 ± 0.02 | 0.35 ± 0.03 |
| Spleen | 0.27 ± 0.01 | 0.27 ± 0.03 |
| Kidneys | 2.23 ± 0.26 | 1.72 ± 0.26 |
| Tumor | 0.56 ± 0.08 | 0.68 ± 0.16 |
| Muscle | 0.054 ± 0.002 | 0.063 ± 0.010 |
| Bone | 0.080 ± 0.005 | 0.077 ± 0.060 |
| Skin | 0.21 ± 0.02 | 0.21 ± 0.03 |
| Stomach & Gut | 0.12 ± 0.01 | |
| Abscess | 0.50 ± 0.07 | 0.55 ± 0.07$^b$ |

$^a$Mean ± S.D. for 5 mice
$^b$Mean ± S.D. for 6 mice
$^c$Mean ± S.D. for 3 mice Following injection of $^{111}$In-BLEDTA III, the blood level of radioactivity in mice is roughly half that observed in a similar experiment with $^{111}$In-BLEDTA I. Lower levels of activity are also observed in the liver and lungs 24 h after injection of $^{111}$In-BLEDTA III. These slight differences in in vivo distribution of radioactivity in mice following injection of $^{111}$In-BLEDTA I and $^{111}$In-BLEDTA III may be due to the extra methylene group present in BLEDTA III.

$^{111}$In-BLEDTA I and $^{111}$In-BLEDTA III both result in almost equal concentrations of radioactivity in tumor tissue and in abscesses, whereas $^{57}$Co-bleomycins concentrate more in tumor tissue than in abscesses.

We claim:

1. A bleomycin analog comprising:
   a modified bleomycin, said bleomycin being modified in one region thereof, said one region being of the structure

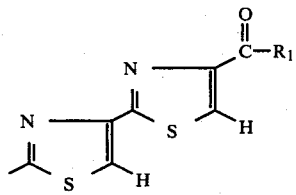

wherein $R_1$ includes a chelating substituent with a plurality of functional groups capable of chelating metal ions.

2. The bleomycin analog as in claim 1, wherein said chelating substituent is an EDTA or a DTPA derivative.

3. The bleomycin analog as in claim 1 wherein said chelating substituent includes a 1-substituted EDTA moiety of the structure

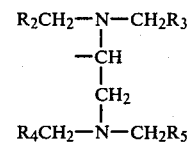

and at least three of $R_2$–$R_5$ are carboxylate moieties as said functional groups.

4. The bleomycin analog as in claim 3 wherein three of $R_2$–$R_5$ are carboxylate moieties as said functional groups, and one of said $R_2$–$R_5$ is —CH$_2$OH.

5. The bleomycin analog as in claim 1 wherein said chelating substituent is a para-substituted, 1-phenyl or 1-benzyl EDTA derivative.

6. The bleomycin analog as in claim 1 wherein said chelating substituent is a 1-(p-acetamidophenyl)-EDTA derivative.

7. The bleomycin analog as in claim 1 wherein said modified bleomycin has another region thereof which is complexed with cobalt or copper.

8. The bleomycin analog as in claim 1 wherein said functional groups are chelated with a metal ion.

9. The bleomycin analog as in 2 wherein said EDTA or DTPA derivative of said chelating substituent is chelated with a radionuclide.

10. The bleomycin analog as in claim 9 wherein said radionuclide emits gamma radiation and has a half-life ranging from about three hours to about three days.

11. The bleomycin analog as in claim 9 wherein said radionuclide is selected from the group consisting of In-111, Tc-99m and Ga-68.

12. The bleomycin analog as in claim 2 wherein said EDTA or DTPA derivative of said chelating substituent is chelated with In-111.

13. A bleomycin analog comprising:
   a bleomycin A$_2$ having a modified terminal amine of the structure

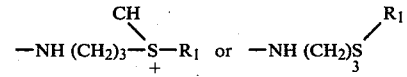

wherein $R_1$ is a chelating substituent with a plurality of functional groups capable of chelating a metal ion.

14. The bleomycin analog as in claim 13 wherein said chelating substituent is an EDTA analog.

15. The bleomycin analog as in claim 13 wherein said chelating substituent includes a 1-substituted EDTA moiety of the structure

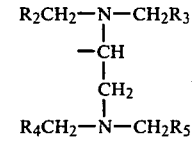

and at least three of $R_2$–$R_5$ are carboxylate moieties as said functional groups.

16. The bleomycin analog as in claim 15 wherein three of $R_2$–$R_5$ are carboxylate moieites as said functional groups and one of said $R_2$–$R_5$ is —$CH_2OH$.

17. The bleomycin analog as in claim 15 wherein said chelating substituent is a para-substituted, 1-phenyl or 1-benzyl EDTA derivative.

18. The bleomycin analog as in claim 13 wherein said functional groups are chelated with a metal ion.

19. A method of localizing tumors in mammals comprising:

providing a quantity of a biologically active bleomycin analog having one region with a 1-substituted EDTA derivative or a DTPA derivative;

exposing said quantity of bleomycin analog to a source of gamma radiation emitting radionuclide, to chelate said radionuclide with amino groups and carboxylate groups of said EDTA or DTPA derivative and to form a radiolabelled bleomycin analog;

injecting a dose of said radiolabelled bleomycin analog into a circulatory system of a mammal; and, scanning the mammal with a gamma detector.

20. The method as in claim 19 wherein said radionuclides are selected from the group consisting of In-111, Tc-99m and Ga-68.

* * * * *

UNITED STATES PATENT AND TRADEMARK OFFICE
CERTIFICATE OF CORRECTION

PATENT NO. : 4,339,426                                      Page 1 of 3
DATED      : July 13, 1982
INVENTOR(S): Meares et al.

It is certified that error appears in the above—identified patent and that said Letters Patent is hereby corrected as shown below:

In the Abstract, Line 7, "meal-" should be --metal--;

Column 8, line 50, "500" should be --50.0--;

Columns 13, 14, Formula 9(d)

"

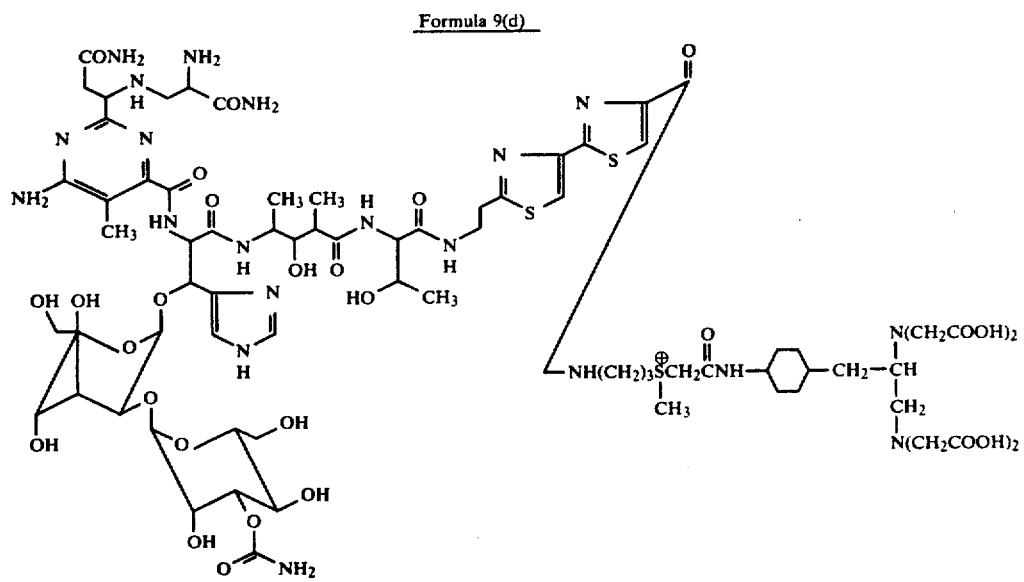

Formula 9(d)

"

should be

UNITED STATES PATENT AND TRADEMARK OFFICE
CERTIFICATE OF CORRECTION

PATENT NO. : 4,339,426

DATED : July 13, 1982

INVENTOR(S) : Meares et al.

It is certified that error appears in the above—identified patent and that said Letters Patent is hereby corrected as shown below:

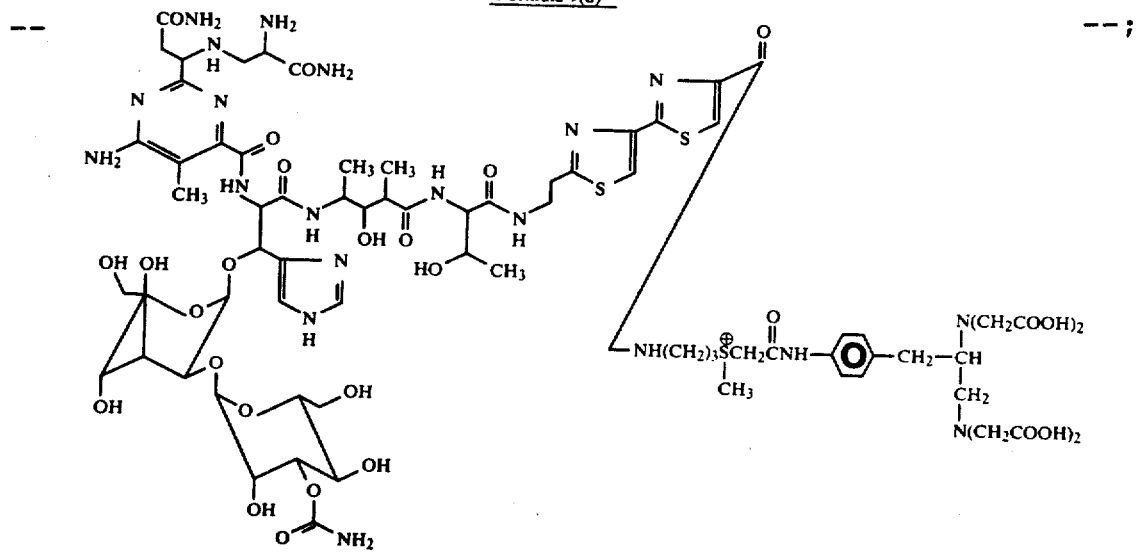

Column 15, line 42, "organic" should be --organ--;

Column 15, line 67, "that or" should be --that of--;

Column 16, line 63, "revealsed" should be --revealed--;

UNITED STATES PATENT AND TRADEMARK OFFICE
CERTIFICATE OF CORRECTION

PATENT NO. : 4,339,426

DATED : July 13, 1982

INVENTOR(S) : Meares et al.

It is certified that error appears in the above—identified patent and that said Letters Patent is hereby corrected as shown below:

Column 20, Claim 13 structure, " 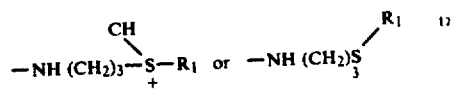 "

should be -- 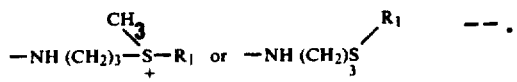 --.

Signed and Sealed this

Fourth Day of January 1983

[SEAL]

Attest:

GERALD J. MOSSINGHOFF

Attesting Officer

Commissioner of Patents and Trademarks